(12) United States Patent
Thewlis et al.

(10) Patent No.: US 7,741,351 B2
(45) Date of Patent: Jun. 22, 2010

(54) COMPOUNDS WHICH POTENTIATE GLUTAMATE RECEPTOR AND USES THEREOF IN MEDICINE

(75) Inventors: Kevin Michael Thewlis, Harlow (GB); Simon Edward Ward, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 598 days.

(21) Appl. No.: 11/573,368

(22) PCT Filed: Aug. 5, 2005

(86) PCT No.: PCT/EP2005/008563

§ 371 (c)(1),
(2), (4) Date: Feb. 7, 2007

(87) PCT Pub. No.: WO2006/015829

PCT Pub. Date: Feb. 16, 2006

(65) Prior Publication Data

US 2007/0203218 A1     Aug. 30, 2007

(30) Foreign Application Priority Data

Aug. 9, 2004    (GB)    .................................. 0417709.3

(51) Int. Cl.
*A61K 31/425*    (2006.01)
*A61K 31/40*     (2006.01)
*A61K 31/275*    (2006.01)
*A61K 31/17*     (2006.01)

(52) U.S. Cl. ........................ 514/372; 514/424; 514/524; 514/597; 514/605; 548/214; 548/550; 558/413; 564/49; 564/99

(58) Field of Classification Search ................. 514/372, 514/424, 524, 597, 605; 548/214, 550; 558/413; 564/49, 99

See application file for complete search history.

(56) References Cited

U.S. PATENT DOCUMENTS 6,525,099 B1 *   2/2003   Arnold et al. ............... 514/605

FOREIGN PATENT DOCUMENTS

| WO | WO 00/06537 A | 2/2000 |
|----|---------------|--------|
| WO | WO 01/42203 A | 6/2001 |

* cited by examiner

*Primary Examiner*—Peter G O'Sullivan
(74) *Attorney, Agent, or Firm*—James M. Kanagy; Edward R. Gimmi; Charles M. Kinzig

(57) ABSTRACT

This case discloses compounds of formula (I) wherein $R^1$ is $C_{1-6}$alkyl, halo$C_{1-6}$alkyl, $C_{2-6}$alkenyl, amino, mono$C_{1-4}$alkylamino or di$C_{1-4}$alkylamino; $R^2$ and $R^3$, which may be the same or different, are hydrogen, halogen, $C_{1-6}$alkyl, halo$C_{1-6}$alkyl, $C_{1-4}$alkoxy, halo$C_{1-4}$alkoxy, cyano or amino; each $R^4$, which may be the same or different, is $C_{1-6}$alkyl, halogen, halo$C_{1-6}$alkyl, $C_{1-4}$alkoxy, halo$C_{1-4}$alkoxy, cyano, nitro or amino; p is 0, 1 or 2; each $R^5$, which may be the same or different, is $C_{1-6}$alkyl, halogen, halo$C_{1-6}$alkyl, $C_{1-4}$alkoxy, halo$C_{1-4}$alkoxy, cyano, nitro or amino; q is 0, 1 or 2; $R^6$ is $-NR^{6a}SO_2R^{6b}$, $-NR^{6a}C(=O)R^{6b}$, $-NR^{6a}(C=O)N(R^{6c})_2$, $-(C=O)R^{6d}$, $-CH_2NR^{6a}SO_2R^{6b}$, $-CH_2NR^{6a}C(=O)R^{6b}$, $CH_2NR^{6a}(C=O)N(R^{6c})_2$ or $-CH_2(C=O)R^{6d}$; where $R^{6a}$ and each $R^{6c}$, which may be the same or different, is hydrogen or $C_{1-6}$alkyl; $R^{6b}$ and $R^{6d}$ are $C_{1-6}$alkyl or halo$C_{1-6}$ alkyl; or $R^{6a}$ and $R^{6b}$, or $R^{6a}$ and $R^{6c}$, together with the interconnecting atoms, may form a 5- or 6-membered ring; n is 1 or 2; and $R^7$ and $R^8$, which may be the same or different, are hydrogen, halogen, $C_{1-6}$alkyl, halo$C_{1-6}$alkyl, $C_{1-4}$alkoxy, halo$C_{1-4}$alkoxy, cyano or amino. It also discloses methods for preparing the compounds and their use in therapy such as treating schizophrenia.

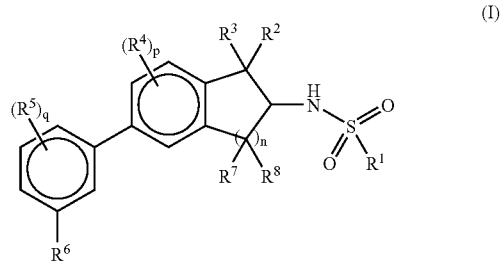

(I)

14 Claims, No Drawings

COMPOUNDS WHICH POTENTIATE GLUTAMATE RECEPTOR AND USES THEREOF IN MEDICINE

This application is a 35 U.S.C. 371 application, which claims the benefit of Provisional Application No. GB0417709.3, filed 9 Aug. 2004.

This invention relates to novel compounds which potentiate the glutamate receptor. The invention also relates to the use of the compounds in treating diseases and conditions mediated by potentiation of the glutamate receptor, compositions containing the compounds and processes for their preparation.

Glutamate receptors, which mediate the majority of fast excitatory neurotransmission in the mammalian central nervous system (CNS), are activated by the excitatory amino acid, L-glutamate (for review see Watkins J C, Krogsgaard-Larsen P, Honore T (1990) Trends Pharmacol Sci 11: 25-33).

Glutamate receptors can be divided into two distinct families. The G-protein or second messenger-linked "metabotropic" glutamate receptor family which can be subdivided into three groups (Group I, mGlu1 and mGlu5; Group II, mGlu2 and mGlu3; Group III, mGlu4, mGlu6, mGlu7, mGlu8) based on sequence homology and intracellular transduction mechanisms (for review see Conn P J and Pinn J P (1997) Ann Rev Pharmacol Toxicol 37: 205-237). The "ionotropic" glutamate receptor family, which directly couple to ligand-gated cation channels, can be subdivided into at least three subtypes based on depolarizing activation by selective agonists, N-methyl-D-aspartate (NMDA), α-amino-3-hydroxy-5-methylisoxazole-4-propionic acid (AMPA) and kainic acid (KA) (for review see Dingledine R, Borges K, Bowie, Traynelis S (1999) 51: 7-61).

Native AMPA receptors (AMPAR) exist as heterotetramers consisting of combinations of four different protein subunits (GluR1-4) (for review see Bettler B and Muller C (1995) 34: 123-139.). Receptor subunit diversity is increased further as each subunit can undergo alternative splicing of a 38 amino acid sequence in the extracellular region just before the fourth membrane spanning domain M4. Such editing results in so-called 'flip' and 'flop' receptor isoforms which differ in kinetic and pharmacological properties (Sommer B, Keinanen K, Verdoon T A, Wisden W, Burnashev N, Herb A, Kohler M, Takagi T, Sakmann B, Seeburg P H (1990) Science 249: 1580-1585).

Additionally, post-transcriptional editing of GluR2 mRNA changes a neutral glutamine to a positively charged arginine within M2. In normal humans >99% GluR2 is edited in this way. AMPAR containing such edited GluR2 subunit exhibit low calcium permeability (Burnachev N, Monyer H, Seeburg P H, Sakmann B (1992) Neuron 8: 189-198). There is a suggestion, however, that the number of AMPAR with high calcium permeability is elevated in certain disease-associated conditions (Weiss J H, and Sensi S L (2000) Trends in Neurosci 23: 365-371.

AMPAR depolarization removes voltage dependent Mg2+ block of NMDA receptors which in turn leads to NMDA receptor activation, an integral stage in the induction of Long Term Potentiation (Bliss T V P, Collingridge G L (1993) Nature 361: 31-9). LTP is a physiological measure of increased synaptic strength following a repetitive stimulus or activity, such as occurs during learning.

Direct activation of glutamate receptors by agonists, in conditions where glutamate receptor function is reduced, increases the risk of excitotoxicity and additional neuronal damage. AMPAR positive allosteric modulators, alone, do not activate the receptor directly. However, when the ligand (L-glutamate or AMPA) is present AMPAR modulators increase receptor activity. Thus, AMPA receptor modulators only enhance synaptic function when glutamate is released and is able to bind at post-synaptic receptor sites.

Compounds which act as AMPAR positive allosteric modulators have been shown to increase ligand affinity for the receptor (Arai A, Guidotti A, Costa E, Lynch G (1996) Neuroreport. 7: 2211-5.); reduce receptor desensitization and reduce receptor deactivation (Arai A C, Kessler M, Rogers G, Lynch G (2000) 58: 802-813) and facilitate the induction of LTP both in vitro (Arai A, Guidotti A, Costa E, Lynch G (1996) 7: 2211-5.) and in vivo (Staubli U, Perez Y, Xu F, Rogers G, Ingvar M, Stone-Elander S, Lynch G (1994) Proc Natl Acad Sci 91: 11158-11162). Such compounds also enhance the learning and performance of various cognitive tasks in rodent (Zivkovic I, Thompson D M, Bertolino M, Uzunov D, DiBella M, Costa E, Guidotti A (1995) JPET 272: 300-309, Lebrun C, Pilliere E, Lestage P (2000) Eu J Pharmacol 401: 205-212), sub-human primate (Thompson D M, Guidotti A, DiBella M, Costa E (1995) Proc Natl Acad Sci 92: 7667-7671) and man (Ingvar M, Ambros-Ingerson J, Davis M, Granger R, Kessler M, Rogers G A, Schehr R S, Lynch G (1997) Exp Neurol 146: 553-559).

It is envisaged that compounds that modulate glutamate receptor function may be useful in treating the following conditions and diseases: psychosis and psychotic disorders (including schizophrenia, schizo-affective disorder, schizophreniform diseases, brief reactive psychosis, child onset schizophrenia, "schizophrenia-spectrum" disorders such as schizoid or schizotypal personality disorders, acute psychosis, alcohol psychosis, drug-induced psychosis, autism, delerium, mania (including acute mania), manic depressive psychosis, hallucination, endogenous psychosis, organic psychosyndrome, paranoid and delusional disorders, puerperal psychosis, and psychosis associated with neurodegenerative diseases such as Alzheimer's disease); cognitive impairment (e.g. the treatment of impairment of cognitive functions including attention, orientation, memory (i.e. memory disorders, amnesia, amnesic disorders and age-associated memory impairment) and language function, and including cognitive impairment as a result of stroke, Alzheimer's disease, Aids-related dementia or other dementia states, as well as other acute or sub-acute conditions that may cause cognitive decline such as delirium or depression (pseudodementia states) trauma, aging, stroke, neurodegeneration, drug-induced states, neurotoxic agents), mild cognitive impairment, age related cognitive impairment, autism related cognitive impairment, Down's syndrome, cognitive deficit related to psychosis, post-electroconvulsive treatment related cognitive disorders; anxiety disorders (including generalized anxiety disorder, social anxiety disorder, agitation, tension, social or emotional withdrawal in psychotic patients, panic disorder, and obsessive compulsive disorder); neurodegenerative diseases (such as Alzheimer's disease, amyotrophic lateral sclerosis, motor neurone disease and other motor disorders such as Parkinson's disease (including relief from locomotor deficits and/or motor disability, including slowly increasing disability in purposeful movement, tremors, bradykinesia, hyperkinesia (moderate and severe), akinesia, rigidity, disturbance of balance and co-ordination, and a disturbance of posture), dementia in Parkinson's disease, dementia in Huntington's disease, neuroleptic-induced Parkinsonism and tardive dyskinesias, neurodegeneration following stroke, cardiac arrest, pulmonary bypass, traumatic brain injury, spinal cord injury or the like, and demyelinating diseases such as multiple sclerosis and amyotrophic lateral sclerosis); depression (which term includes bipolar (manic) depression (including type I and type II), unipolar depression, single or recurrent major depressive episodes with or without psychotic features, catatonic features, melancholic features, atypical features (e.g. lethargy, over-eating/obesity, hypersomnia) or postpartum onset, seasonal affective disorder and dysthymia, depression-related anxiety, psychotic depression, and depressive disorders resulting from a general medical condition including, but not limited to, myocardial infarction, diabetes, miscarriage or abortion); post-traumatic stress syndrome; attention deficit disorder; attention deficit hyperactivity disorder; drug-induced (phencyclidine, ketamine and other dissociative anaesthetics, amphetamine and other psychostimulants and cocaine) disorders; Huntingdon's chorea; tardive dyskinesia; dystonia; myoclonus; spasticity; obesity; stroke; sexual dysfunction; and sleep disorders. In addition, it is envisaged that compounds that modulate glutamate receptor function may be useful in treating non-impaired subjects for enhancing performance in sensory-motor and cognitive tasks and memory encoding.

We have discovered a class of novel compounds that potentiate the glutamate receptor.

According to a first aspect, the invention provides a compound of formula (I), a pharmaceutically acceptable salt, solvate or prodrug thereof:

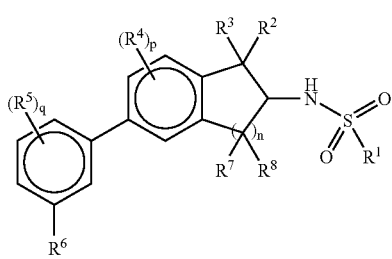

(I)

wherein
$R^1$ is $C_{1-6}$alkyl, halo$C_{1-6}$alkyl, $C_{2-6}$alkenyl, amino, mono$C_{1-4}$alkylamino or di$C_{1-4}$alkylamino;
$R^2$ and $R^3$, which may be the same or different, are hydrogen, halogen, $C_{1-6}$alkyl, halo$C_{1-6}$alkyl, $C_{1-4}$alkoxy, halo$C_{1-4}$alkoxy, cyano or amino;
each $R^4$, which may be the same or different, is $C_{1-6}$alkyl, halogen, halo$C_{1-6}$alkyl, $C_{1-4}$alkoxy, halo$C_{1-4}$alkoxy, cyano, nitro or amino; p is 0, 1 or 2;
each $R^5$, which may be the same or different, is $C_{1-6}$alkyl, halogen, halo$C_{1-6}$alkyl, $C_{1-4}$alkoxy, halo$C_{1-4}$alkoxy, cyano, nitro or amino; q is 0, 1 or 2;
$R^6$ is —$NR^{6a}SO_2R^{6b}$, —$NR^{6a}C(=O)R^{6b}$, —$NR^{6a}(C=O)N(R^{6c})_2$, —$(C=O)R^{6d}$, —$CH_2NR^{6a}SO_2R^{6b}$, —$CH_2NR^{6a}C(=O)R^{6b}$, —$CH_2NR^{6a}(C=O)N(R^{6c})_2$ or —$CH_2(C=O)R^{6d}$; where $R^{6a}$ and each $R^{6c}$, which may be the same or different, is hydrogen or $C_{1-6}$alkyl; $R^{6b}$ and $R^{6d}$ are $C_{1-6}$alkyl or halo$C_{1-6}$alkyl; or $R^{6a}$ and $R^{6b}$, or $R^{6a}$ and $R^{6c}$, together with the interconnecting atoms, may form a 5- or 6-membered ring;
n is 1 or 2; and
$R^7$ and $R^8$, which may be the same or different, are hydrogen, halogen, $C_{1-6}$alkyl, halo$C_{1-6}$alkyl, $C_{1-4}$alkoxy, halo$C_{1-4}$alkoxy, cyano or amino.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "$C_{1-6}$alkyl" refers to an alkyl group having from one to six carbon atoms, in all isomeric forms, such as methyl, ethyl, propyl, isopropyl, butyl, isobutyl, sec-butyl, tert-butyl, pentyl, neopentyl, sec-pentyl, n-pentyl, iso-pentyl, tert-pentyl and hexyl. Unless otherwise indicated, any alkyl group may be straight or branched and is of 1 to 6 carbon atoms, such as 1 to 4 or 1 to 3 carbon atoms.

The term "halo" refers to fluoro, chloro, bromo or iodo.

The term "halo$C_{1-6}$alkyl" refers to a $C_{1-6}$alkyl group wherein at least one hydrogen atom is replaced with halogen. Examples of such groups include fluoroethyl, trifluoromethyl or trifluoroethyl and the like.

The term "$C_{2-6}$alkenyl" refers to a straight or branched hydrocarbon group containing one or more carbon-carbon double bonds and having from 2 to 6 carbon atoms. Unless otherwise indicated, a $C_{2-6}$alkenyl group may contain up to 3 double bonds which may be conjugated. Examples of such groups include ethenyl, propenyl, butenyl, pentenyl, hexenyl, vinyl, allyl and butadienyl.

Halo is fluoro, chloro, bromo or iodo.

In one embodiment, $R^1$ is $C_{1-6}$alkyl such as isopropyl.

In one embodiment, $R^2$ and $R^3$, which may be the same or different, are hydrogen, halogen or $C_{1-6}$alkyl, such as hydrogen, fluorine or methyl.

In one embodiment, when present, each $R^4$, which may be the same or different, is $C_{1-6}$alkyl or halogen, such as methyl or fluorine.

In one embodiment, when present, each $R^5$, which may be the same or different, is $C_{1-6}$alkyl or halogen.

In one embodiment, n is 1.

In one embodiment, $R^7$ and $R^8$, which may be the same or different, are hydrogen, halogen or $C_{1-6}$alkyl; such as hydrogen, fluorine or methyl.

In one embodiment, the present invention provides a compound of formula (Ia), a pharmaceutically acceptable salt, solvate or prodrug thereof:

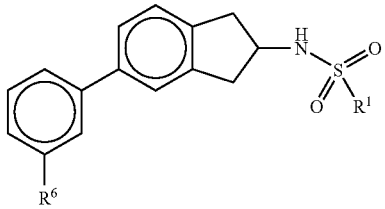

(Ia)

wherein $R^6$ and $R^1$ are as defined for formula (I).

It will be appreciated that the present invention is intended to include compounds having any combination of the above features.

For the avoidance of doubt, unless otherwise indicated, the term "substituted" means substituted by one or more defined groups. In the case where groups may be selected from a number of alternative groups, the selected groups may be the same or different. For the avoidance of doubt, the term "independently" means that where more than one substituent is selected from a number of possible substituents, those substituents may be the same or different.

Suitable pharmaceutically acceptable salts of the compounds of formula (I) include acid salts, for example sodium, potassium, calcium, magnesium and tetraalkylammonium and the like, or mono- or di-basic salts with the appropriate acid for example organic carboxylic acids such as formic, acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids and the like. Some of the compounds of this invention may be crystallized or recrystallized from solvents such as aqueous and organic solvents. In such cases solvates may be formed. This invention includes within its scope stoichiometric solvates including hydrates as well as compounds containing variable amounts of water that may be produced by processes such as lyophilisation.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolized in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. Examples of suitable protecting groups for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Hereinafter, compounds, their pharmaceutically acceptable salts, their solvates and prodrugs, defined in any aspect of the invention (except Intermediate compounds in chemical processes) are referred to as "compounds of the invention".

The compounds of the invention may exist in one or more tautomeric forms. All tautomers and mixtures thereof are included in the scope of the present invention.

Compounds of the invention may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses.

Due to the presence of at least one chiral centre, the compounds of the invention may exist in the form of optical isomers, e.g. diastereoisomers and mixtures of isomers in all ratios, e.g. racemic mixtures:

R form

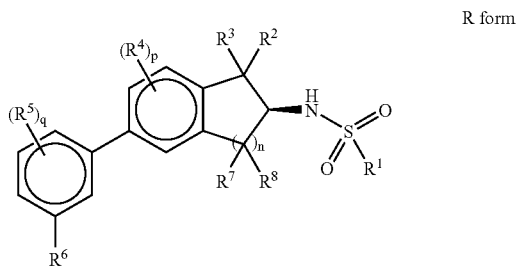

-continued

S form

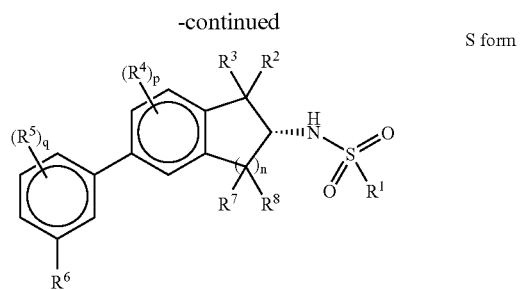

The invention includes all such forms, in particular the pure isomeric forms. The different isomeric forms may be separated or resolved one from the other by conventional methods, or any given isomer may be obtained by conventional synthetic methods or by stereospecific or asymmetric syntheses. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In a further embodiment of the present invention, compounds of formula (Ib) or a pharmaceutically acceptable salt, solvate or prodrug thereof are provided which correspond to a stereochemical isomer of compounds of formula (I), enriched in configuration S:

(Ib)

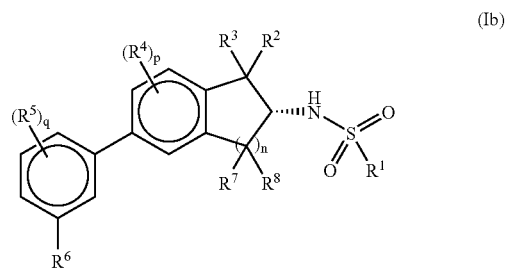

wherein $R^1$, $R^2$, $R^3$, $R^4$, $R^5$, $R^6$, $R^7$, $R^8$, p, q and n are as defined for formula (I).

In another embodiment, the present invention provides a compound of formula (Ic) or a pharmaceutically acceptable salt, solvate or prodrug thereof which correspond to a stereochemical isomer of compounds of formula (Ia), enriched in configuration S:

(Ic)

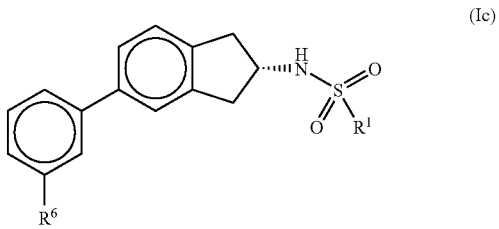

wherein $R^5$, $R^6$ and $R^1$ are as defined for formula (I).

It is intended in the context of the compounds of the present invention that stereochemical isomers enriched in configuration S correspond in one embodiment to at least 90% enantiomeric excess. In another embodiment the isomers correspond to at least 95% enantiomeric excess. In another embodiment the isomers correspond to at least 99% enantiomeric excess.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Example compounds of formula (I) include:

N-(5-{4-[(methylsulfonyl)amino]phenyl}-2,3-dihydro-1H-inden-2-yl)-2-propanesulfonamide N-[3-(2-{[(1-methylethyl)sulfonyl]amino}-2,3-dihydro-1H-inden-5-yl)phenyl]acetamide N-[5-(3-acetylphenyl)-2,3-dihydro-1H-inden-2-yl]-2-propanesulfonamide N-(5-{3-[methyl(methylsulfonyl)amino]phenyl}-2,3-dihydro-1H-inden-2-yl)-2-propanesulfonamide N-[5-(3-{[(ethylamino)carbonyl]amino}phenyl)-2,3-dihydro-1H-inden-2-yl]-2-propanesulfonamide N-(5-{3-[(ethylsulfonyl)amino]phenyl}-2,3-dihydro-1H-inden-2-yl)-2-propanesulfonamide 2-methyl-N-[3-(2-{[(1-methylethyl)sulfonyl]amino}-2,3-dihydro-1H-inden-5-yl)phenyl]propanamide N-{5-[3-(2-oxopropyl)phenyl]-2,3-dihydro-1H-inden-2-yl}-2-propanesulfonamide N-[5-(3-cyanophenyl)-2,3-dihydro-1H-inden-2-yl]-2-propanesulfonamide N-{5-[3-(aminomethyl)phenyl]-2,3-dihydro-1H-inden-2-yl}-2-propanesulfonamide N-[5-(3-{[(methylsulfonyl)amino]methyl}phenyl)-2,3-dihydro-1H-inden-2-yl]-2-propanesulfonamide N-{[3-(2-{[(1-methylethyl)sulfonyl]amino}-2,3-dihydro-1H-inden-5-yl)phenyl]methyl}acetamide N-(5-{3-[(2-oxo-1-pyrrolidinyl)methyl]phenyl}-2,3-dihydro-1H-inden-2-yl)-2-propanesulfonamide N-{5-[3-(1,1-dioxido-2-isothiazolidinyl)phenyl]-2,3-dihydro-1H-inden-2-yl}-2-propanesulfonamide N-(5-{3-[(methylsulfonyl)methyl]phenyl}-2,3-dihydro-1H-inden-2-yl)-2-propanesulfonamide 3-(2-{[dihydroxy(1-methylethyl)-$\lambda^4$-sulfanyl]amino}-2,3-dihydro-1H-inden-5-yl)-N,N-dimethylbenzenesulfonamide 3-(2-{[dihydroxy(1-methylethyl)-$\lambda^4$sulfanyl]amino}-2,3-dihydro-1H-inden-5-yl)benzenesulfonamide and pharmaceutically acceptable salts, solvates and prodrugs thereof.

Compounds of the invention may be prepared, in known manner in a variety of ways. In the following reaction schemes and hereafter, unless otherwise stated $R^1$ to $R^8$, n, p and q are as defined in the first aspect. These processes form further aspects of the invention.

Throughout the specification, general formulae are designated by Roman numerals (I), (II), (III), (IV) etc. Subsets of these general formulae are defined as (Ia), (Ib), (Ic) etc . . . . (IVa), (IVb), (IVc) etc.

Compounds of general formula (I) may be prepared by reacting compounds of formula (II) where X is a leaving group such as iodine, with boronic acid or boronate ester derivatives of formula (III) where R is hydrogen, alkyl or two R groups combine to form a ring, according to reaction scheme 1. Typical coupling conditions comprise reacting (II) with (III) in the presence of a base (such as aqueous cesium carbonate), a palladium (II) catalyst and triphenylphosphine at elevated temperature (such as 80 deg C.).

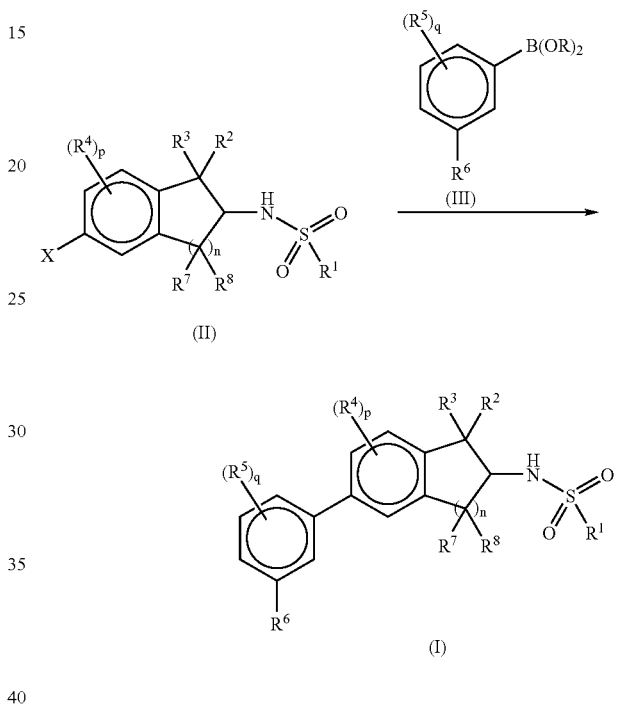

Scheme 1

Alternatively compounds of formula (Id), i.e. compounds of general formula (I) where $R^6$ is —$NR^{6a}(C=O)N(R^{6a})_2$, may be prepared from compounds of formula (IV) according to reaction scheme 2, by reacting compounds of formula (IV) with compounds of formula (V). Typical reaction conditions comprise adding isocyanate (V) to an ice-cooled mixture of (IV) and a base (such as diisopropylamine) in a suitable solvent (such as dichloromethane) and then warming the mixture gradually to room temperature.

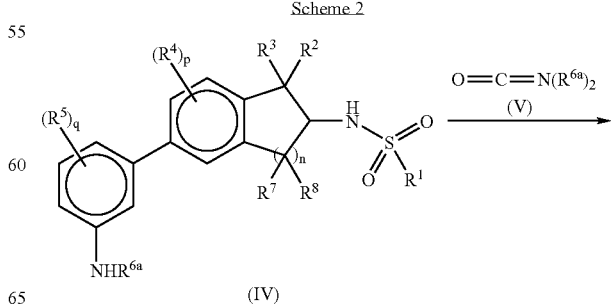

Scheme 2

-continued

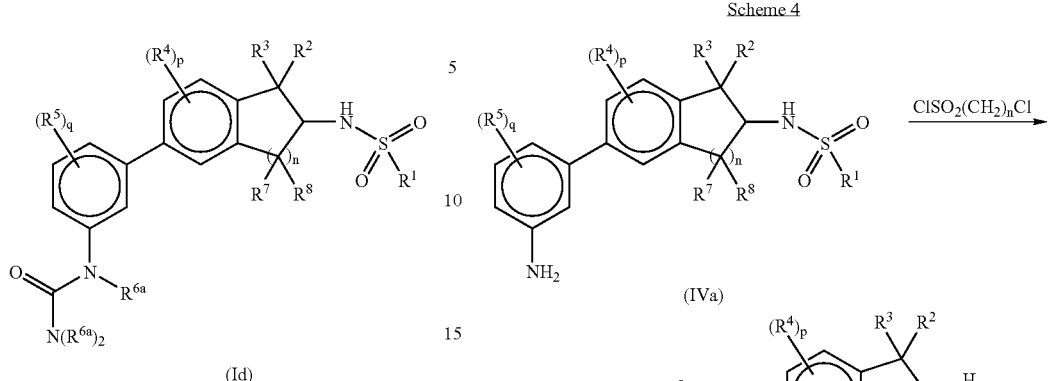
(Id)

Compounds of formula (Ie), i.e. compounds of general formula (I) where $R^6$ is —$NR^{6a}SO_2R^{6b}$, may be prepared from compounds of formula (IV) according to reaction scheme 3. Typical reaction conditions comprise adding sulfonyl chloride (VI) to an ice-cooled mixture of (IV) and a base (such as diisopropylamine) in a suitable solvent (such as dichloromethane) and then warming the mixture gradually to room temperature.

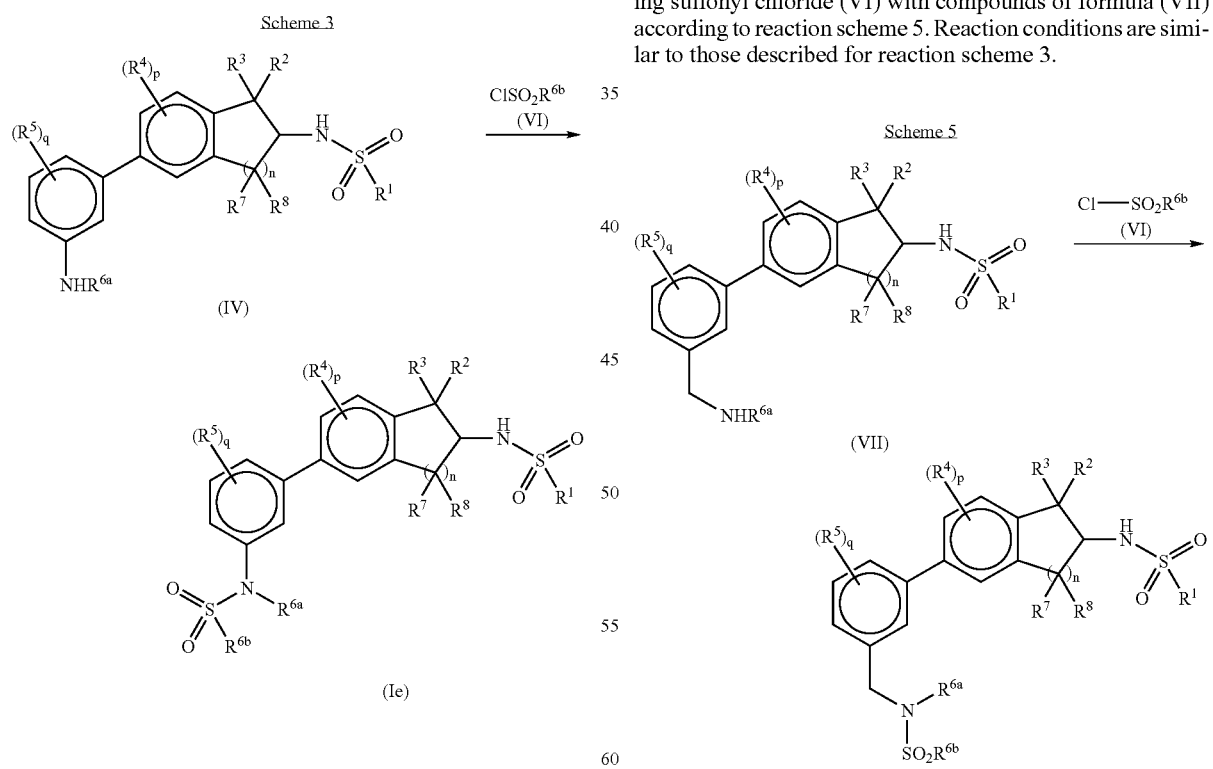

Compounds of formula (If), i.e. compounds of general formula (I) where $R^6$ is —$NR^{6a}SO_2R^{6b}$ wherein $R^{6a}$ and $R^{6b}$ together make up a ring, may be prepared from compounds of formula (IVa) using a doubly electrophilic sulfonyl chloride such as $Cl(CH_2)_nSO_2Cl$, under similar conditions to Scheme 3 (see Scheme 4).

Compounds of formula (Ig), i.e. compounds of formula (I) where $R^6$ is —$CH_2NR^{6a}SO_2R^{6b}$, may be prepared by reacting sulfonyl chloride (VI) with compounds of formula (VII) according to reaction scheme 5. Reaction conditions are similar to those described for reaction scheme 3.

The boronic acid or boronate ester derivatives of formula (III) (see reaction scheme 1) may be prepared from aryl halides of formula (VIII) where Hal is typically iodine, bromine or chlorine according to reaction scheme 6. Typical reaction conditions comprise reacting (VIII) with boronate (IX) in the presence of a base (such as aqueous cesium carbonate), a palladium (II) catalyst and triphenylphosphine at elevated temperature (such as 80° C.).

Scheme 6

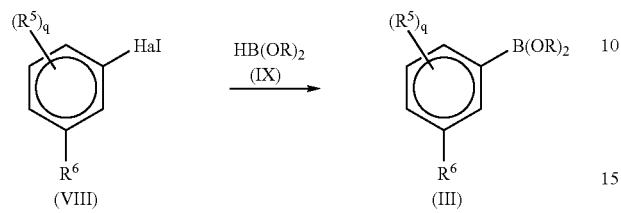

Compounds of formula (IIa) (see reaction scheme 1), i.e. compounds of formula (II) where X is iodine, may be prepared from compounds of formula (X) according to reaction scheme 7. Typical reaction conditions require treatment of (X) with strong acid such as sulfuric acid and glacial acetic acid followed by treatment with periodic acid and iodine.

Scheme 7

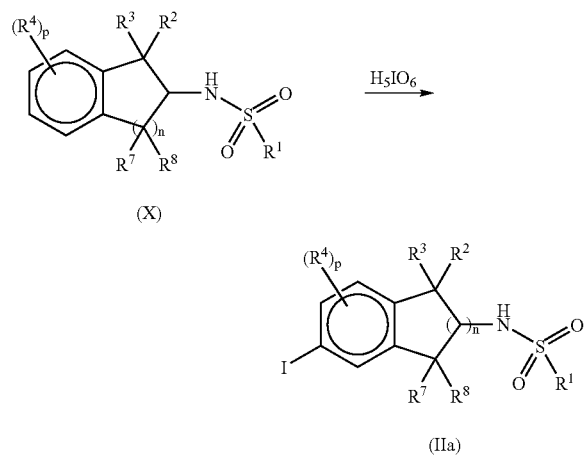

Compounds of formula (X) may be prepared from compounds of formula (XI) according to reaction scheme 8. Typical reaction conditions are adding sulfonyl chloride (XII) to an ice-cooled mixture of (XI) and a base (such as diisopropylamine) in a suitable solvent (such as dichloromethane) and then warning the mixture gradually to room temperature.

Scheme 8

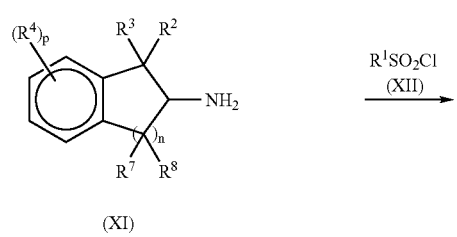

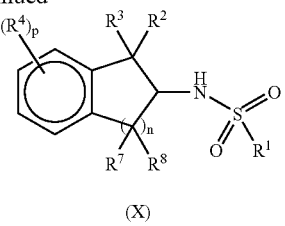

(X)

Compounds of formula (XI) may be prepared from compounds of formula (XIII) (see reaction scheme 9) by standard procedures such as described in Synlett 1999, 1781.

Scheme 9

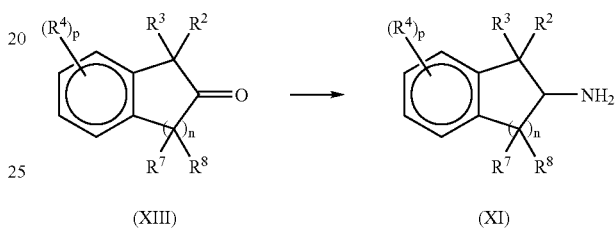

Compounds of formula (XIII) where at least one of $R^2$, $R^3$, $R^7$ or $R^8$ is other than hydrogen, may be prepared according to reaction scheme 10 from compounds of formula (XIV) by synthetic procedures known in the art, followed by suitable purification, typically chromatography. For example, when $R^2$, $R^3$, $R^7$ or $R^8$ is alkyl, typical reaction conditions comprise stirring an ice-cooled solution of (XIV) in suitable solvent (such as tetrahydrofuran) followed by consecutive treatment with a base such as sodium hydride and an alkylating agent such as an alkyl halide. Alternatively, when $R^2$, $R^3$, $R^7$ or $R^8$ is fluoro, typical reaction conditions comprise reacting (XIV) with a standard flurorinating agent such as Accuflour™ in a solvent such as acetonitrile (see Tetrahedron Letters 1996, 3591). When $R^2$, $R^3$, $R^7$ or $R^8$ is bromo, typical reaction conditions comprise stirring an ice-cooled solution of (XIV) in a suitable solvent (such as tetrahydrofuran) followed by consecutive treatment with a base such as sodium hydride and an brominating agent such as N-bromosuccinimide. It will be appreciated by the skilled chemist that these bromo intermediates can by further converted into the corresponding hydroxy/alkoxy compounds by treatment with the sodium hydroxide/sodium alkoxide respectively in a suitable solvent such as tetrahydrofuran.

Scheme 10

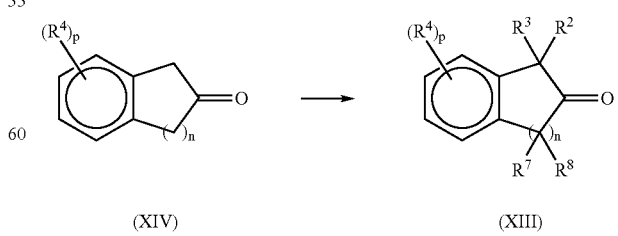

Alternative preparation of compounds of structure (XIII) are described in Organic Letters 2002, 2465.

Compounds of formula (VIIa) (see reaction scheme 5) may be prepared from compounds of formula (XV) according to reaction scheme 11 using standard conditions reduction conditions such as lithium aluminium hydride or a borane complex in an inert aprotic solvent such as tetrahydrofuran.

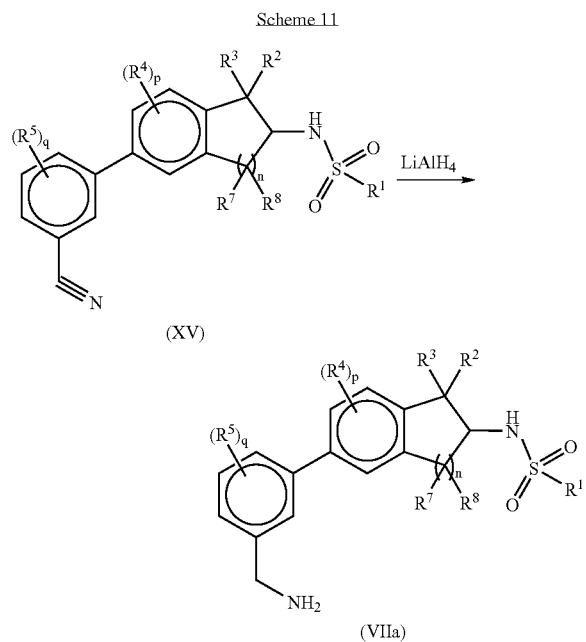

Further details for the preparation of compounds of formula (I) are found in the examples section hereinafter.

Thus, in another aspect, the present invention provides a process for preparing a compound as defined in claim 1, comprising reacting a compound of formula (II):

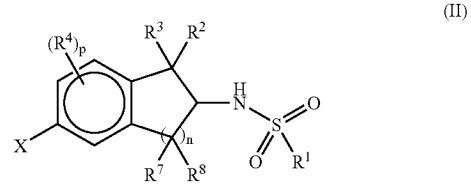

wherein $R^1$ to $R^4$, $R^7$, $R^8$, n and p are as defined for formula (I) and X is a leaving group; with a boronic acid or boronate ester derivative compound of formula (III):

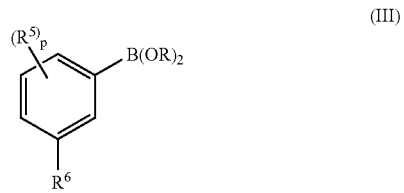

wherein $R^5$, $R^6$, and q is as defined for formula (I), and R is hydrogen, alkyl (such as $C_{1-6}$alkyl) or two R groups form a ring (such as a 5 or 6 membered ring);

and thereafter optionally:
  removing any protecting group(s); and/or
  forming a salt; and/or
  converting one compound of formula (I) to a different compound of formula (I).

The compounds of the invention may be prepared singly or as compound libraries comprising at least 2, for example 5 to 1,000 compounds, and more preferably 10 to 100 compounds. Libraries of compounds of the invention may be prepared by a combinatorial 'split and mix' approach or by multiple parallel synthesis using either solution phase or solid phase chemistry, by procedures known to those skilled in the art. Thus according to a further aspect there is provided a compound library comprising at least 2 compounds of the invention.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

It will be recognized by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e. the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The preferred embodiments described for the first aspect extend these further aspects:

i) a pharmaceutical composition comprising a compound of the invention and a pharmaceutically acceptable carrier or diluent;

ii) the use of a compound of the invention in the manufacture of a medicament for treating or preventing a disease or condition caused by a reduction or imbalance in glutamate receptor function in a mammal;

iii) a compound of the invention for use in treating or preventing a disease or condition caused by a reduction or imbalance in glutamate receptor function in a mammal;

iv) a compound of the invention for use as a medicament;

v) a method of treatment or prevention of a disease or condition caused by a reduction or imbalance in glutamate receptor function in a mammal comprising administering an effective amount of a compound of the invention; and vi) a combination of a compound of the invention with an antipsychotic.

In the case of aspects ii), iii) and v), relevant diseases or conditions are: psychosis and psychotic disorders (including schizophrenia, schizo-affective disorder, schizophreniform diseases, brief reactive psychosis, child onset schizophrenia, "schizophrenia-spectrum" disorders such as schizoid or schizotypal personality disorders, acute psychosis, alcohol psychosis, drug-induced psychosis, autism, delerium, mania (including acute mania), manic depressive psychosis, hallucination, endogenous psychosis, organic psychosyndrome, paranoid and delusional disorders, puerperal psychosis, and psychosis associated with neurodegenerative diseases such as Alzheimer's disease); cognitive impairment (e.g. the treatment of impairment of cognitive functions including attention, orientation, memory (i.e. memory disorders, amnesia, amnesic disorders and age-associated memory impairment) and language function, and including cognitive impairment as a result of stroke, Alzheimer's disease, Aids-related dementia or other dementia states, as well as other acute or sub-acute conditions that may cause cognitive decline such as delirium or depression (pseudodementia states) trauma, aging, stroke, neurodegeneration, drug-induced states, neurotoxic agents), mild cognitive impairment, age related cognitive impairment, autism related cognitive impairment, Down's syndrome, cognitive deficit related to psychosis, post-electroconvulsive treatment related cognitive disorders; anxiety disorders (including generalized anxiety disorder, social anxiety disorder, agitation, tension, social or emotional withdrawal in psychotic patients, panic disorder, and obsessive compulsive disorder); neurodegenerative diseases (such as Alzheimer's disease, amyotrophic lateral sclerosis, motor neurone disease and other motor disorders such as Parkinson's disease (including relief from locomotor deficits and/or motor disability, including slowly increasing disability in purposeful movement, tremors, bradykinesia, hyperkinesia (moderate and severe), akinesia, rigidity, disturbance of balance and co-ordination, and a disturbance of posture), dementia in Parkinson's disease, dementia in Huntington's disease, neuroleptic-induced Parkinsonism and tardive dyskinesias, neurodegeneration following stroke, cardiac arrest, pulmonary bypass, traumatic brain injury, spinal cord injury or the like, and demyelinating diseases such as multiple sclerosis and amyotrophic lateral sclerosis); depression (which term includes bipolar (manic) depression (including type I and type II), unipolar depression, single or recurrent major depressive episodes with or without psychotic features, catatonic features, melancholic features, atypical features (e.g. lethargy, over-eating/obesity, hypersomnia) or postpartum onset, seasonal affective disorder and dysthymia, depression-related anxiety, psychotic depression, and depressive disorders resulting from a general medical condition including, but not limited to, myocardial infarction, diabetes, miscarriage or abortion); post-traumatic stress syndrome; attention deficit disorder; attention deficit hyperactivity disorder; drug-induced (phencyclidine, ketamine and other dissociative anaesthetics, amphetamine and other psychostimulants and cocaine) disorders; Huntingdon's chorea; tardive dyskinesia; dystonia; myoclonus; spasticity; obesity; stroke; sexual dysfunction; and sleep disorders.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes:

Schizophrenia including the subtypes Paranoid Type (295.30), Disorganized Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-induced Psychotic Disorder including the subtypes With Delusions (293.81) and With Hallucinations (293.82); and Psychotic Disorder Not Otherwise Specified (298.9).

Compounds of formula (I) and pharmaceutically acceptable salts and solvates thereof may also be of use in the treatment of the following disorders:

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-induced Anxiety Disorder, Separation Anxiety Disorder (309.21), Adjustment Disorders with Anxiety (309.24) and Anxiety Disorder Not Otherwise Specified (300.00):

Substance-related disorders including Substance Use Disorders such as Substance Dependence, Substance Craving and Substance Abuse; Substance-Induced Disorders such as Substance Intoxication, Substance Withdrawal, Substance-induced Delirium, Substance-induced Persisting Dementia, Substance-induced Persisting Amnestic Disorder, Substance-induced Psychotic Disorder, Substance-induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-induced Persisting Dementia, Alcohol-Induced Persisting Amnestic Disorder, Alcohol-induced Psychotic Disorder, Alcohol-Induced Mood Disorder, Alcohol-induced Anxiety Disorder, Alcohol-induced Sexual Dysfunction, Alcohol-induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-induced Mood Disorder, Amphetamine-Induced Anxiety Disorder, Amphetamine-Induced Sexual Dysfunction, Amphetamine-induced Sleep Disorder and Amphetamine-Related Disorder Not Otherwise Specified (292.9); Caffeine Related Disorders such as Caffeine Intoxication (305.90), Caffeine-induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-induced Psychotic Disorder, Cannabis-induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-induced Psychotic Disorder, Cocaine-induced Mood Disorder, Cocaine-Induced Anxiety Disorder, Cocaine-induced Sexual Dysfunction, Cocaine-induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-induced Mood Disorder, Hallucinogen-induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-induced Persisting Dementia, Inhalant-induced Psychotic Disorder, Inhalant-Induced Mood Disorder, Inhalant-induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as NightmareDisorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-induced Sleep Disorder including the subtypes Insomnia Type, Hypersomnia Type, Parasomnia Type and Mixed Type; sleep apnea and jet-lag syndrome:

Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9):

Enhancement of cognition including the treatment of cognition impairment in other diseases such as schizophrenia, bipolar disorder, depression, other psychiatric disorders and psychotic conditions associated with cognitive impairment, e.g. Alzheimer's disease: and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

All of the various forms and sub-forms of the disorders mentioned herein are contemplated as part of the present invention.

Within the context of the present invention, the term "cognitive impairment" includes for example the treatment of impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

The compounds of the invention may be used in combination with the following agents to treat or prevent psychotic disorders: i) antipsychotics (such as olanzapine, risperidone, clozapine, ziprazidone and talnetant); ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilizers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example lofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyroheptidine; ii) antidepressants; iii) antipsychotics; iv) zinc; and v) premenstrual agents for example pyridoxine and progesterones.

The compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilizers; vi) zinc; and vii) premenstrual agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent Attention Deficit Hyperactivity Disorder: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilizers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone, amisulpride, ziprazidone and talnetant).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabilizer drugs include lithium, sodium valproate/valproic acid/divalproex, carbamazepine, lamotrigine, gabapentin, topiramate and tiagabine.

Anxiolytics include benzodiazepines such as alprazolam and lorazepam.

EXAMPLES

The invention is illustrated by the Examples described below.

Starting materials were obtained from commercial suppliers and used without further purification unless otherwise stated. Flash chromatography was carried out using pre-packed Isolute Flash™ or Biotage™ silica-gel columns as the stationary phase and analytical grade solvents as the eluent. Catch and release purification was carried out using SCX (strong cation exchanger) cartridges, consisting of bonded-phase silica with sulfonic acid functional groups. Mass directed preparative HPLC was carried out using a 19 mm×100 mm or 30 mm×100 mm, 5 µm, reversed phase Waters Atlantis column as the stationary phase and a gradient from water +0.1% formic acid to acetonitrile +0.1% formic acid as the eluent. The eluent was monitored by a Waters 996 photodiode array and a Micromass ZQ mass spectrometer. All yields reported are of purified, isolated material. NMR spectra were obtained at 298K, at the frequency stated using either a Bruker™ DPX400 or an Oxford Instruments™ 250 MHz machine and run as a dilute solution of $CDCl_3$ unless otherwise stated. All NMR spectra were reference to tetramethylsilane (TMS $\delta_H$ 0, $\delta_C$ 0). All coupling constants are reported in hertz (Hz), and multiplicities are labelled s (singlet), bs, (broad singlet), d (doublet), t (triplet), q (quartet), dd (doublet of doublets), dt (doublet of triplets) and m (multiplet).

LC/MS (Liquid Chromatography/Mass Spectrometry) data were obtained using an Agilent™ 1100 HPLC system with a 4.6 mm×50 mm, 3 µm, reversed phase Waters Atlantis™ column as the stationary phase. A gradient elution from 97% water+0.05% formic acid/3% acetonitrile+0.05% formic acid to 97% acetonitrile+0.05% formic acid over 3 minutes plus a further minute continuing this mixture at a flow rate of 1.5 mL/min was used as the eluent. Retention time is reported as minutes (with percentage intensity for DA/ELSD for the relevant peak). Spectroscopic monitoring was performed using an Agilent™ 1100 diode array (DA) detector or a Sedex™ evaporative light scattering detector (ELSD). Total ion current traces were obtained for electrospray positive and negative ionisation (ES+/ES−) and atmospheric pressure chemical positive and negative ionisation (AP+/AP−).

Intermediate 1:
N-(2,3-dihydro-1H-inden-2-yl)-2-propanesulfonamide

2-Aminoindan hydrochloride (5.16 g, 30 mmol, Sigma Aldrich Company Ltd.) was suspended in dry dichloromethane (100 ml), and cooled with stirring under argon to 0° C. To the suspension was added 1,8-diazabicyclo[5.4.0]undec-7-ene (14 g, 92 mmol) followed by the dropwise addition of isopropylsulfonyl chloride (8.56 g, 60 mmol). The cooling bath was removed and the mixture stirred at room temperature for 1 h. The reaction mixture was diluted with dichloromethane (50 ml) and washed with 1 M hydrochloric acid (2×50 ml). The organic layer was separated, dried over sodium sulphate and evaporated under reduced pressure to give a yellow oil (11.8 g). The crude product was purified by chromatography on a 50 g Isolute™ Flash silica-gel column eluting from 20-50% ethyl acetate in 40-60° C. petroleum ether to give the title compound as a pale yellow solid (6.88 g, 96%); $^1$H-NMR (400 MHz, CDCl$_3$) δ 1.39 (6H, d, J=7 Hz), 2.91 (2H, m), 3.18 (1H, m), 3.31 (2H, m), 4.31 (2H, m), 7.21 (4H, m).

Intermediate 2: N-(5-iodo-2,3-dihydro-1H-inden-2-yl)-2-propanesulfonamide

Intermediate 1 (1.75 g, 7.32 mmol) was dissolved in glacial acetic acid (30 ml) and then treated with concentrated sulfuric acid (0.8 ml) followed by water (2.8 ml) with stirring. This mixture was then treated with periodic acid (0.38 g, 1.67 mmol) then iodine (800 mg, 3.15 mmol), and the whole mix was stirred at 60° C. for 4 h. The reaction mixture was allowed to cool and then partitioned between ethyl acetate (150 ml) and 10% aqueous sodium metabisulfite (100 ml). The organic layer was separated and dried over sodium sulphate and evaporated in vacuo to give the title compound as a yellow oil (2.67 g, 100%); mass spectrum: Found 364 (MH$^-$), $C_{12}H_{16}INO_2S$ requires 365; $^1$H-NMR (400 MHz, CDCl$_3$) δ 1.39 (6H, m), 3.39 (2H, m), 3.18 (1H, m), 3.28 (2H, m), 4.38 (1H, m), 4.63 (1H, m), 6.97 (1H, d, J=8 Hz), 7.51 (1H, m), 7.56 (1H, m).

Intermediate 3: N-[5-(3-nitrophenyl)-2,3-dihydro-1H-inden-2-yl]-2-propanesulfonamide A mixture of Intermediate 2 (800 mg, 2.19 mmol) and 3-nitrophenyl boronic acid (366 mg, 2.19 mmol, Sigma Aldrich Company Ltd.) in dioxane (60 ml) was treated with cesium carbonate (1.07 g, 3.29 mmol) and water (20 ml) and degassed with argon for 2 min. Palladium (II) acetate (25 mg, 0.11 mmol) and triphenylphosphine (58 mg, 0.22 mmol) were added and the mixture was stirred at 80° C. under argon for 16 h. The reaction mixture was cooled, then partitioned between ethyl acetate (100 ml) and water (100 ml). The organic layer was separated and dried over Na$_2$SO$_4$ and evaporated in vacuo to give a brown oil (861 mg). This crude oil was purified using flash chromatography to give the title compound as a yellow oil (500 mg, 63%); mass spectrum: (ES$^-$): Found 359 (MH$^-$). $C_{18}H_{20}N_2O_4S$ requires 360; $^1$H-NMR (400 MHz, CDCl$_3$) δ 1.38 (6H, m), 2.99 (2H, m), 3.18 (1H, m), 3.38 (2H, m), 4.35 (2H, m), 7.34 (1H, d J=8 Hz), 7.45 (2H, m), 7.60 (1H, m), 7.88 (1H, dd, J=8 Hz and 1 Hz), 8.19 (1H, m), 8.41 (1H, m).

Intermediate 4: N-[5-(3-aminophenyl)-2,3-dihydro-1H-inden-2-yl]-2-propanesulfonamide A solution of Intermediate 3 (430 mg, 1.19 mmol) in ethanol (10 ml) was treated with 10% palladium on charcoal (paste) (100 mg), and then stirred under an atmosphere of hydrogen at room temperature and pressure for 24 h. The mixture was filtered through a bed of kieselguhr and washed through with ethanol. The filtrate was removed under reduced pressure to give the title compound as a colourless solid (320 mg, 81%); mass spectrum: (ES$^-$): Found 329 (MH$^-$); $C_{18}H_{22}N_2O_2S$ requires 330; $^1$H-NMR (400 MHz, CDCl$_3$) δ 1.36 (6H, m), 2.94 (2H, m), 3.17 (1H, m), 3.35 (2H, m), 3.77 (2H, bs), 4.31 (2H, m), 6.67 (1H, m), 6.87 (1H, m), 6.95 (1H, m), 7.22 (2H, m), 7.39 (2H, m).

Intermediate 5: N-(3-bromophenyl)-N-methylmethanesulfonamide

A solution of N-(3-bromophenyl)methanesulfonamide (5.15 g, 20.6 mmol, Combi-Blocks) in dry dimethylformamide (100 ml) was treated with potassium carbonate (4.3 g, 31.2 mmol) at room temperature with stirring under argon. After stirring for 10 minutes methyl iodide (2.9 g, 20.6 mmol) was added dropwise over 5 minutes and stirring continued at room temperature for 1 h. The reaction mixture was partitioned between ethyl acetate (250 ml), and water (3×150 ml). The organic layer was dried over sodium sulphate and the solvent removed under reduced pressure to give the title compound as a brown oil (4.90 g, 90%); $^1$H-NMR (400 MHz, CDCl$_3$): 2.86 (3H, s), 3.32 (3H, s), 7.26 (1H, m), 7.35 (1H, m), 7.43 (1H, m), 7.53 (1H, m).

Intermediate 6: N-methyl-N-[3-(4,4,5,5-tetramethyl-1,3,2-dioxaborolan-2-yl)phenyl]methanesulfonamide A mixture of (1,1'-bis(diphenylphosphino)ferrocene)palladium(II) chloride complex with dichloromethane (32 mg, 0.044 mmol), potassium acetate (432 mg, 4.41 mmol), and bis(pinacolato)diboron (411 mg, 1.62 mmol) in dimethylsulfoxide (9 ml) was degassed with argon for 5 mins. A solution of Intermediate 5 (388 mg, 1.47 mmol) in dimethylsulfoxide (5 ml) was added and the resulting mixture stirred at 80° C. for 3 h. The reaction mixture was allowed to cool and diluted with ethyl acetate (25 ml). This solution was washed with water (3×15 ml). The organic layer was separated, dried over anhydrous sodium sulfate and evaporated under reduced pressure to give a dark oil (0.66 g) which was chromatographed on a 5 g Isolute™ Flash silica-gel column, eluting from 0-50% ethyl acetate in 40-60° C. petroleum ether to give the title compound as a brown oil (0.40 g, 87%); $^1$H-NMR (400 MHz, CDCl$_3$): 1.35 (12H, s), 2.89 (3H, s), 3.39 (3H, s), 7.38 (1H, m), 7.49 (1H, m), 7.58 (1H, m), 7.73 (1H, m).

Intermediate 7: (3-bromophenyl)methyl methyl sulfone

A solution of 3-bromobenzyl bromide (5.0 g, 20 mmol) in dry dimethylformamide (50 ml) at room temperature under an atmosphere of argon was treated portionwise with sodium methanesulfinate (2.0 g, 20 mmol) with stirring. The mixture was stirred at room temperature for 16 h, and then at 50° C. for 0.5 h. The reaction mix was allowed to cool to room temperature and then partitioned between ethyl acetate and water. The organic layer was separated and dried over sodium sulfate and the solvent removed under reduced pressure to give an oil which was purified by column chromatography on a 50 g isolute silica sep-pak column eluting from 0-100% ethyl acetate in petroleum ether to give the title compound as an off-white solid (3.34 g, 67%).

1H-NMR (400 MHz, CDCl$_3$): 2.80 (3H, s), 4.22 (2H, s), 7.30 (1H, t, J=8 Hz), 7.37 (1H, m), 7.56 (2H, m).

Intermediate 8: N-[5-(4,4,5,5-tetramethyl-1,3,2-dioxaborolan-2-yl)-2,3-dihydro-1H-inden-2-yl]-2-propanesulfonamide A mixture of (1,1'-bis(diphenylphosphino)ferrocene)palladium(II) chloride complex with dichloromethane (3 mol %, 200 mg, 0.27 mmol), potassium acetate (2.64 g, 26.9 mmol), and bis(pinacolato)diboron (1.1 eq., 2.3 g, 9.1 mmol) in dimethylsulfoxide (60 ml) was degassed with argon for 5 mins. A solution of _N-(5-iodo-2,3-dihydro-1H-inden-2-yl)-2-propanesulfonamide (3.0 g, 8.22 mmol) in dimethylsulfoxide (20 ml) was added and the resulting mixture stirred at 80° C. under argon for 3 h. The reaction mixture was allowed to cool and diluted with ethyl acetate. This solution was washed with water (3×). The organic layer was separated, dried over sodium sulfate and evaporated under reduced pressure to give a dark oil (3.25 g) which was purified by chromatography on a 50 g Isolute™ Flash silica-gel column, eluting from 0-50% ethyl acetate in petroleum ether to give the title compound as a brown oil (2.60 g, 87%).

Mass spectrum (API−): Found 364 (MH−), $C_{18}H_{28}BNO_4S$ requires 365; $^1$H-NMR (250 MHz, $CDCl_3$): δ 1.34 (12H, s), 1.39 (6H, d, J=7 Hz), 2.90 (2H, m), 3.18 (1H, m), 3.32 (2H, m), 4.27 (2H, m), 7.26 (1H, m), 7.65 (2H, m).

Example 1

N-(5-{4-[(methylsulfonyl)amino]phenyl}-2,3-dihydro-1H-inden-2-yl)-2-propanesulfonamide

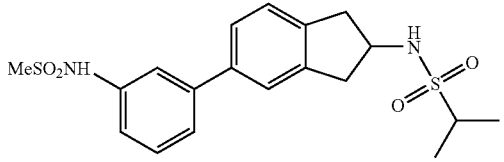

A mixture of Intermediate 2 (400 mg, 1.08 mmol) and 3-methylsulfonamide phenyl boronic acid (352 mg, 1.62 mmol, Combi-Blocks) in dioxane (50 ml) was treated with cesium carbonate (536 mg, 1.62 mmol) and water (15 ml) and degassed with argon for 2 min. Palladium (II) acetate (12 mg, 0.05 mmol) and triphenylphosphine (56 mg, 0.22 mmol) were added and the mixture was stirred at 80° C. under argon for 16 h. The reaction mixture was cooled, then partitioned between ethyl acetate (50 ml) and water (50 ml). The organic layer was separated and dried over $Na_2SO_4$ and evaporated in vacuo to give a brown oil (703 mg). This crude oil was purified using flash chromatography to give the title compound as a white solid (136 mg, 30%); mass spectrum (ES−): Found 407 (MH−). $C_{19}H_{24}N_2O_4S_2$ requires 408; $^1$H-NMR (400 MHz, $CDCl_3$) δ 1.39 (6H, d, J=7 Hz), 2.97 (2H, m), 3.05 (3H, s), 3.21 (1H, m), 3.37 (2H, m), 4.34 (1H, m), 6.52 (1H, bs), 7.18 (1H, m), 7.24 (1H, m,), 7.29 (1H, d, J=7 Hz), 7.40 (4H, m).

Example 2

N-[3-(2-{[(1-methylethyl)sulfonyl]amino}-2,3-dihydro-1H-inden-5-yl)phenyl]acetamide

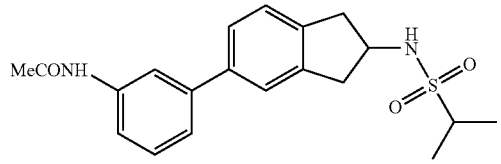

The title compound was prepared from Intermediate 2 and 3-(acetylamino)phenyl]boronic acid (Sigma Aldrich Company Ltd.) using the method of Example 1; mass spectrum (API+): Found 373 (MH+), $C_{20}H_{24}N_2O_3S$ requires 372; 1H-NMR (400 MHz, $CDCl_3$): 1.41 (6H, d, J=7 Hz), 2.20 (3H, s), 2.96 (2H, m), 3.20 (1H, m), 3.34 (2H, m), 4.33 (1H, m), 4.41 (1H, m), 7.23 (2H, m), 7.38 (5H, m), 7.74 (1H, m).

Example 3

N-[5-(3-acetylphenyl)-2,3-dihydro-1H-inden-2-yl]-2-propanesulfonamide

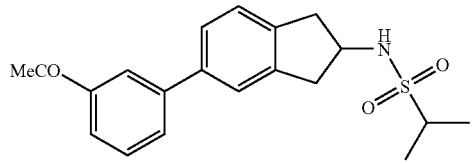

The title compound was prepared from Intermediate 2 and (3-acetylphenyl)boronic acid (Sigma Aldrich Company Ltd.) using the method of Example 1; mass spectrum (API+): Found 358 (MH+), $C_{20}H_{23}NO_3S$ requires 357; $^1$H-NMR (400 MHz, $CDCl_3$): 1.42 (6H, d, J=7 Hz), 2.66 (3H, s), 2.99 (2H, m), 3.20 (1H, m), 3.35 (2H, m), 4.29 (2H, m), 7.32 (1H, m), 7.46 (2H, m), 7.56 (1H, m), 7.76 (1H, m), 7.92 (1H, m), 8.14 (1H, m).

Example 4

N-(5-{3-[methyl(methylsulfonyl)amino]phenyl}-2,3-dihydro-1H-inden-2-yl)-2-propanesulfonamide

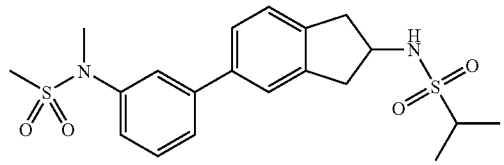

The title compound was prepared from Intermediates 2 and 6 using the method of Example 1; mass spectrum (ES): Found 421 (ES−), $C_{20}H_{26}N_2O_4S_2$ requires 422; $^1$H-NMR (400 MHz, $CDCl_3$): 1.41 (6H, d, J=7 Hz), 2.88 (3H, s), 2.97 (2H, m), 3.20 (1H, m), 3.37 (5H, m), 4.32 (2H, m), 7.30 (3H, m), 7.45 (4H, m).

Example 5

N-[5-(3-{[(ethylamino)carbonyl]amino}phenyl)-2,3-dihydro-1H-inden-2-yl]-2-propanesulfonamide

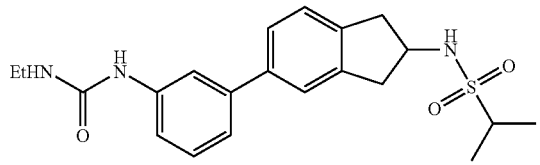

A solution of Intermediate 4 (45 mg, 0.14 mmol), and diisopropylethylamine (36 mg, 0.28 mmol) in dry dichloromethane (3 ml) was cooled to 0° C. using an ice/methanol bath. Ethyl isocyanate (10 mg, 0.14 mmol) was added with stirring under argon and the whole mixture stirred at room temperature for 1 h. The reaction mixture was partitioned between dichloromethane (5 ml) and 1N hydrochloric acid (5 ml). The organic layer was removed and reduced to minimum volume under reduced pressure. The crude mixture was purified by flash column chromatography eluting from 0-50% ethyl acetate in 40-60° C. petroleum ether to give the title compound as a colourless oil (13 mg, 24%); mass spectrum (ES): Found 400 (ES$^-$), $C_{21}H_{27}N_3O_3S$ requires 401; $^1$H-NMR (400 MHz, CDCl$_3$) δ 1.16 (3H, m), 1.38 (6H, m), 2.93 (2H, m), 3.19 (1H, m), 3.32 (4H, m), 4.32 (1H, m), 4.44 (1H, m), 4.82 (1H, m), 6.48 (1H, s), 7.23 (3H, m), 7.36 (3H, m), 7.54 (1H, m).

Example 6

N-(5-{3-[(ethylsulfonyl)amino]phenyl}-2,3-dihydro-1H-inden-2-yl)-2-propanesulfonamide

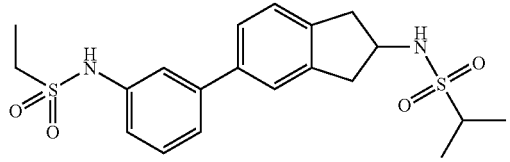

The title compound was prepared from Intermediate 4 and ethane sulfonyl chloride using the method of Example 4; mass spectrum (API): Found 421 (MH−), $C_{20}H_{26}N_2O_4S_2$ requires 422; $^1$H-NMR (400 MHz, CDCl$_3$): 1.42 (9H, m), 2.98 (2H, m), 3.18 (3H, m), 3.37 (2H, m), 4.36 (2H, m), 7.21 (2H, m), 7.29 (1H, m), 7.39 (4H, m).

Example 7

2-methyl-N-[3-(2-{[(1-methylethyl)sulfonyl]amino}-2,3-dihydro-1H-inden-5-yl)phenyl]propanamide

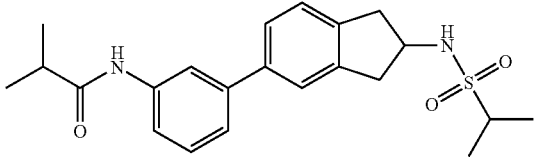

The title compound was prepared from Intermediate 4 and isopropyl sulfonyl chloride using the method of Example 4; mass spectrum (API+): Found 399 (MH−), $C_{22}H_{28}N_2O_3S$ requires 400; $^1$H-NMR (400 MHz, CDCl$_3$): 1.28 (6H, m), 1.41 (6H, d, J=7 Hz), 2.54 (1H, m), 2.96 (2H, m), 3.20 (1H, m), 3.36 (2H, m), 4.34 (2H, m), 7.28 (3H, m), 7.37 (4H, m), 7.85 (1H, m).

Example 8

N-{5-[3-(2-oxopropyl)phenyl]-2,3-dihydro-1H-inden-2-yl}-2-propanesulfonamide

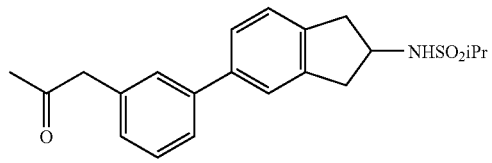

The title compound was prepared from N-[5-(4,4,5,5-tetramethyl-1,3,2-dioxaborolan-2-yl)-2,3-dihydro-1H-inden-2-yl]-2-propanesulfonamide and 1-(3-bromophenyl)-2-propanone in a similar manner to Example 1.

Mass Spectrum (ES): Found 370 (ES−). $C_{21}H_{25}NO_3S$ requires 371.

$^1$H-NMR (400 MHz, CDCl3): 1.40 (6H, m), 2.20 (3H, s), 2.96 (2H, m), 3.20 (1H, m), 3.36 (2H, m), 3.76 (2H, s), 4.34 (1H, m), 4.46 (1H, m), 7.18 (1H, m), 7.26 (2H, m), 7.43 (4H, m).

Example 9

N-[5-(3-cyanophenyl)-2,3-dihydro-1H-inden-2-yl]-2-propanesulfonamide

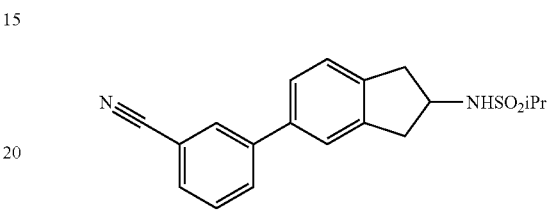

The title compound was prepared from N-(5-iodo-2,3-dihydro-1H-inden-2-yl)-2-propanesulfonamide and 3-cyanophenyl boronic acid in a similar manner to Example 1.

Mass Spectrum (ES): Found 339 (ES−). $C_{19}H_{20}N_2O_2S$ requires 340.

$^1$H-NMR (400 MHz, CDCl3): 1.41 (6H, d, J=7 Hz), 2.98 (2H, m), 3.21 (1H, m), 3.38 (2H, m), 4.37 (2H, m), 7.32 (1H, d, J=8 Hz), 7.39 (2H, m), 7.53 (1H, m), 7.62 (1H, m), 7.78 (1H, m), 7.83 (1H, m).

Example 10

N-{5-[3-(aminomethyl)phenyl]-2,3-dihydro-1H-inden-2-yl}-2-propanesulfonamide

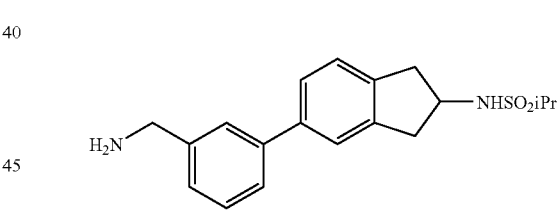

A 1.0M solution of lithium aluminium hydride in tetrahydrofuran (8 ml) was cooled to 0° C. in an ice/methanol bath with stirring under argon. The solution was then treated dropwise with a solution of N-[5-(3-cyanophenyl)-2,3-dihydro-1H-inden-2-yl]-2-propanesulfonamide (0.67 g, 1.97 mmol) in dry tetrahydrofuran (20 ml) over 15 mins. The cooling bath was removed and the whole mix stirred at reflux for 2 h. The reaction mix was allowed to cool to room temperature and quenched with water (0.8 ml), 10% NaOH (0.8 ml), and water again (1.2 ml). The reaction mix was dried over sodium sulphate, filtered and the filtrate evaporated under reduced pressure to give the title compound as a yellow oil (0.67 g, 100%).

Mass Spectrum (ES): Found 345 (ES+). $C_{19}H_{24}N_2O_2S$ requires 344.

$^1$H-NMR (400 MHz, CDCl3): 1.40 (6H, d, J=7 Hz), 1.66 (2H, m), 2.96 (2H, m), 3.19 (1H, m), 3.36 (2H, m), 3.91 (2H, m), 4.33 (1H, m), 4.67 (1H, m), 7.27 (2H, m), 7.40 (4H, m), 7.49 (1H, s).

Example 11

N-[5-(3-{[(methylsulfonyl)amino]methyl}phenyl)-2,3-dihydro-1H-inden-2-yl]-2-propanesulfonamide

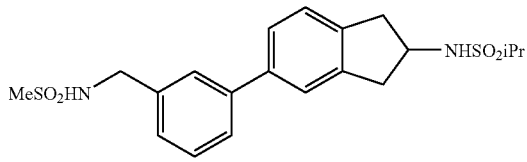

A solution of N-{5-[3-(aminomethyl)phenyl]-2,3-dihydro-1H-inden-2-yl}-2-propanesulfonamide (69 mg, 0.2 mmol) in dichloromethane (5 ml) was treated with triethylamine (40 mg, 0.4 mmol), followed by methanesulfonyl chloride (25 mg, 0.22 mmol) and the wole mix stirred at room temperature under argon for 1 h. The reaction mix was washed with 0.5M hydrochloric acid, and the organic layer was evaporated under reduced pressure to give a brown oil which was purified by column chromatography on a 1 g SCX column eluting from 0-50% ethyl acetate in 40-60° C. petroleum ether to give the title compound as a yellow oil (46 mg, 55%).

Mass Spectrum (ES): Found 421 (ES−). $C_{20}H_{26}N_2O_4S_2$ requires 422.

$^1$H-NMR (250 MHz, CDCl3): 1.40 (6H, d, J=7 Hz), 2.91 (3H, s), 2.97 (2H, m), 3.20 (1H, m), 3.36 (2H, m), 4.37 (4H, m), 4.75 (1H, m), 7.30 (2H, m), 7.42 (3H, m), 7.52 (2H, m).

Example 12

N-{[3-(2-{[(1-methylethyl)sulfonyl]amino}-2,3-dihydro-1H-inden-5-yl)phenyl]methyl}acetamide

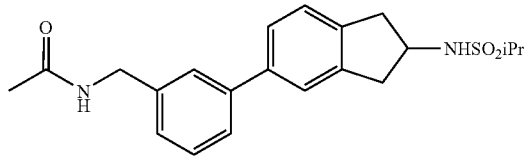

The title compound was prepared from N-{5-[3-(aminomethyl)phenyl]-2,3-dihydro-1H-inden-2-yl}-2-propanesulfonamide and acetyl chloride in a similar manner to Example 12.

Mass Spectrum (ES): Found 385 (ES−). $C_{21}H_{26}N_2O_3S$ requires 386.

$^1$H-NMR (250 MHz, CDCl3): 1.40 (6H, m), 2.04 (3H, s), 2.96 (2H, m), 3.20 (1H, m), 3.34 (2H, m), 4.41 (3H, m), 4.49 (2H, s), 7.26 (2H, m), 7.42 (5H, m).

Example 13

N-(5-{3-[(2-oxo-1-pyrrolidinyl)methyl]phenyl}-2,3-dihydro-1H-inden-2-yl)-2-propanesulfonamide

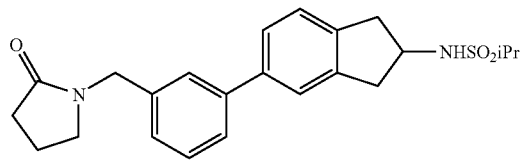

A solution of N-{5-[3-(aminomethyl)phenyl]-2,3-dihydro-1H-inden-2-yl}-2-propanesulfonamide (69 mg, 0.2 mmol) in dichloromethane (5 ml) was treated with triethylamine (40 mg, 0.4 mmol), followed by 4-chlorobutanoyl chloride (32 mg, 0.22 mmol) and the whole mix stirred at room temperature under argon for 1 h. The reaction mix was evaporated under reduced pressure to remove the dichloromethane and then dimethylformamide was added (5 ml) followed by potassium carbonate (60 mg, 0.43 mmol) and the mix stirred at 100° C. for 2 h. The reaction mix was cooled then partitioned between dichloromethane and 0.5M hydrochloric acid, and the organic layer was evaporated under reduced pressure to give a brown oil which was purified by column chromatography on a 1 g SCX column eluting from 0-50% ethyl acetate in 40-60° C. petroleum ether to give the title compound as a beige solid (16 mg, 19%).

Mass Spectrum (ES): Found 413 (ES+). $C_{23}H_{28}N_2O_3S$ requires 412.

$^1$H-NMR (400 MHz, CDCl3): 1.41 (6H, d, J=7 Hz), 2.00 (2H, m), 2.45 (2H, m), 2.96 (2H, m), 3.21 (1H, m), 3.30 (2H, m), 3.38 (2H, m), 4.35 (2H, m), 4.51 (2H, s), 7.22 (1H, m), 7.28 (1H, d, J=8 Hz), 7.40 (4H, m)., 7.47 (1H, m).

Example 14

N-{5-[3-(1,1-dioxido-2-isothiazolidinyl)phenyl]-2,3-dihydro-1H-inden-2-yl}-2-propanesulfonamide

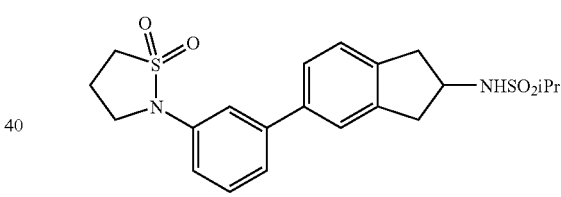

A mixture of N-[5-(3-aminophenyl)-2,3-dihydro-1H-inden-2-yl]-2-propanesulfonamide (100 mg, 0.30 mmol), and diisopropylethylamine (79 mg, 0.61 mmol), in dry dimethylformamide (2 ml) was treated with 3-chloropropanesulfonyl chloride (54 mg, 0.30 mmol) and stirred at room temperature for 1 h. Sodium hydride (60% dispersion in oil, 15 mg, 0.38 mmol) was added and the mixture stirred at 60° C. for 0.5 h. The reaction mix was cooled then partitioned between dichloromethane and 0.5M hydrochloric acid, and the organic layer was evaporated under reduced pressure to give a brown oil which was purified by column chromatography on a 5 g isolute silica sep-pak column eluting from 0-50% ethyl acetate in 40-60° C. petroleum ether to give the title compound as a yellow oil (12 mg, 9%).

Mass Spectrum (ES): Found 433 (ES−). $C_{21}H_{26}N_2O_4S_2$ requires 434.

$^1$H-NMR (400 MHz, CDCl3): 1.41 (6H, d, J=7 Hz,), 2.56 (2H, m), 2.95 (2H, m), 3.20 (1H, m), 3.36 (2H, m), 3.41 (2H, t, J=8 Hz), 3.84 (2H, m), 4.32 (2H, m), 7.23 (1H, m), 7.27 (1H, m), 7.32 (1H, m), 7.39 (4H, m).

Example 15

N-(5-{3-[(methylsulfonyl)methyl]phenyl}-2,3-dihydro-1H-inden-2-yl)-2-propanesulfonamide

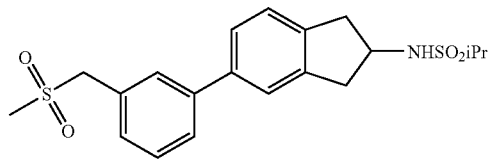

The title compound was prepared from N-[5-(4,4,5,5-tetramethyl-1,3,2-dioxaborolan-2-yl)-2,3-dihydro-1H-inden-2-yl]-2-propanesulfonamide and (3-bromophenyl)methyl methyl sulfone in a similar manner to Example 16.

Mass Spectrum (ES): Found 406 (ES−). $C_{20}H_{25}NO_4S_2$ requires 407.

$^1$H-NMR (400 MHz, CDCl3): 1.41 (6H, d, J=7 Hz), 2.80 (3H, s), 2.97 (2H, m), 3.20 (1H, m), 3.37 (2H, m), 4.30 (2H, m), 4.36 (2H, m), 7.29 (1H, d, J=8 Hz), 7.44 (5H, m), 7.60 (1H, m).

Example 16

3-(2-{[dihydroxy(1-methylethyl)-$\lambda^4$-sulfanyl]amino}-2,3-dihydro-1H-inden-5-yl)-N,N-dimethylbenzenesulfonamide

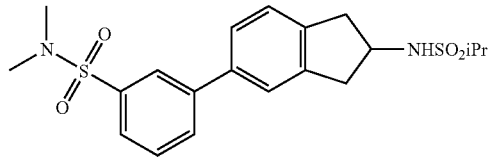

The title compound was prepared from N-(5-iodo-2,3-dihydro-1H-inden-2-yl)-2-propanesulfonamide and {3-[(dimethylamino)sulfonyl]phenyl}boronic acid (WO2003004472) in a similar manner to Example 1.

Mass Spectrum (ES): Found 421 (ES−). $C_{20}H_{26}N_2O_4S_2$ requires 422.

$^1$H-NMR (400 MHz, CDCl3): 1.41 (6H, d, J=7 Hz), 2.75 (6H, s), 2.99 (2H, m), 3.21 (1H, m), 3.38 (2H, m), 4.37 (2H, m), 7.32 (1H, d, J=8 Hz), 7.43 (2H, m), 7.60 (1H, m), 7.76 (2H, m), 7.95 (1H, m).

Example 17

3-(2-{[dihydroxy(1-methylethyl)-$\lambda^4$-sulfanyl]amino}-2,3-dihydro-1H-inden-5-yl)benzenesulfonamide

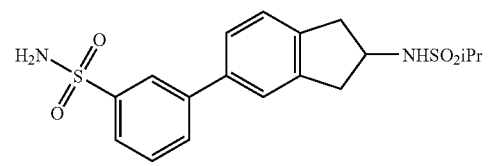

The title compound was prepared from N-(5-iodo-2,3-dihydro-1H-inden-2-yl)-2-propanesulfonamide and [3-(aminosulfonyl)phenyl]boronic acid (WO2003004472) in a similar manner to Example 1.

Mass Spectrum (ES): Found 393 (ES−). $C_{18}H_{22}N_2O_4S_2$ requires 394.

$^1$H-NMR (400 MHz, CDCl3): 1.41 (6H, m), 2.98 (2H, m), 3.21 (1H, m), 3.39 (2H, m), 4.27 (1H, m), 4.35 (1H, m), 4.81 (2H, bs), 7.32 (1H, m), 7.42 (2H, m), 7.60 (1H, m), 7.79 (1H, m), 7.90 (1H, m), 8.14 (1H, m).

Biological Assay

The ability of the compounds of the invention to potentiate glutamate receptor-mediated response were determined a) by using fluorescent calcium-indicator dyes such as FLUO4 and b) by measuring glutamate-evoked current recorded from human GluR2 flip unedited HEK293 cells.

a) Calcium Influx Fluorescence Assay 384 well plates were prepared containing confluent monolayer of HEK 293 cells either stably expressing or transiently transfected with human GluR2 flip (unedited) AMPA receptor subunit. These cells form functional homotetrameric AMPA receptors. The tissue culture medium in the wells was discarded and the wells were each washed three times with standard buffer (80 μL) for the stable cell line (145 mM NaCl, 5 mM KCl, 1 mM $MgCl_2$, 2 mM $CaCl_2$, 20 mM N-[2-hydroxyethyl]-piperazine-N-[2-ethanesulfonic acid (HEPES), 5.5 mM glucose, pH 7.3) or with a Na-free buffer for the transient transfected cells (145 mM N-methyl-glucamine instead of NaCl). The plates were then incubated for 60 minutes in the dark with 2 μM FLUO4-AM dye (Molecular Probes, Netherlands) at room temperature to allow cell uptake of the FLUO-4AM, which is then converted to FLUO-4 by intracellular esterases which is unable to leave the cell. After incubation each well was washed three times with buffer (80 μL) (30 μL of buffer remained in each well after washing).

Compounds of the invention (or reference compounds such as cyclothiazide) were dissolved in dimethylsulfoxide (DMSO) at a stock concentration of 10 mM. These solutions were further diluted with DMSO using a Biomek FX (Beckman Coulter) in a 384 compound plate. Each dilution (1 μL) was transferred to another compound plate and buffer (50 μL) was added. An agonist stimulus (glutamate) plate was prepared by dissolving sodium glutamate in water to give a concentration of 100 mM. This solution was diluted with buffer to give a final concentration of 500 μM and dispensed into another 384-well plate (50 μL/well) using a Multidrop (Thermolabsystems).

The cell plate was then transferred into a fluorescence imaging plate based reader [such as the FLIPR384 (Molecular Devices)]. A baseline fluorescence reading was taken over a 10 to 240 second period, and then 10 μL from each plate containing a compound of the invention made up in standard buffer solution (in a concentration range from 100 μM to 10 pM) was added (to give a final concentration in the range 30 μM to 3 pM). The fluorescence was read over 5 minute period. 500 μM glutamate solution (10 μL) was added (to give a final concentration of 100 μM). The fluoresecence was then read over a 4 minute period. The activities of the compounds of the invention and reference compounds were determined by measuring peak fluorescence after the last addition. The activity can also be expressed relative to the fluorescence increase induced by cyclothiazide at their maximum response (i.e. greater than 30 μM).

All examples were screened using Assay a). Using Assay a), all examples gave a pEC$_{50}$ equal to or greater than 4.3. Some compounds gave a pEC$_{50}$ equal to or greater than 4.9. Example 6 gave a pEC$_{50}$ of 5.5.

b) Whole Cell Voltage-Clamp Electrophysiology Assay

This assay involved the electrophysiological characterization of AMPA receptor positive modulators using HEK293 cells stably expressing human GluR2 flip (unedited) subunits which form a functional homotetrameric AMPA receptor. The extracellular recording solution contained 135 mM NaCl, 2 mM KCl, 1 mM MgCl$_2$, 2 mM CaCl$_2$, 12 mM N-[2-hydroxyethyl]-piperazine-N-[2-ethanesulfonic acid (HEPES), 10 mM D-glucose, pH 7.35. The intracellular solution contained (150 mM CsCl, 10 mM N-[2-hydroxyethyl]-piperazine-N-[2-ethanesulfonic acid (HEPES), 2 mM ethylene glycol-bis(g-aminoethylether)-N,N,N',N,-tetra-acetic acid (EGTA), pH 7.3. Intracellular solution containing amphotericin B (240 μg/ml) was used to backfill the pipette while intracellular solution alone was used to fill just the tip (the patch clamp pipettes have a resistance of between 2-5 MΩ). Amphoteracin B creates small pores in the cell membrane beneath the electrode which allow small ions to pass across the membrane (and therefore allow electrical control of the cell) without the dialysis of second messenger molecules out of the cell, which could result in metabolic rundown of the cell leading to inconsistent receptor activiton (Virginio C, Giacometti A, Aldegheri L, Rimland J M, Terstappen G C (2002) Eur J Pharmacol 445: 153-161) The membrane potential of the cell was held at −60 mV and perforated-patch clamp electrophysiology performed using HEKA hard- and software (Germany). The cell was positioned in front of the first of 16 linearlly arranged channels. The system moves one channel then the next in front of a single patch-clamped cell allowing rapid exchange and precise application times of solutions (for more information see http://www.cellectricon.se/). The first channel contained normal buffer for baseline current measurement. The second channel contained 3 mM glutamate which was applied to the cell for 500 ms to record a control (agonist alone) response. The third channel contained normal buffer which washed off glutamate for 1 to 3 min. The fourth channel contained either a compound of the invention or a reference compound was moved in front of the cell for one minute. The fifth channel contained glutamate in the presence of the test (or reference) compound which was applied to the cell for 500 ms. The sixth channel contained normal buffer which washed off the glutamate plus test (or reference) compound for 1 to 3 min. This procedure was repeated for increasing concentrations of either a compound of the invention or a reference compound.

The activity of a compound of the invention is determined by measuring the peak current amplitude or the area under the curve (500 ms) for the glutamate response in the presence of a compound of the invention (or reference) and expressed it as % of potentiation of the glutamate alone response (glutamate in the absence of the compound of the invention (or reference compound).

Alternatively, the activity can be expressed as the activity of glutamate in the presence of the compound of the invention (or reference compound) relative to the response induced by glutamate in the presence of cyclothiazide at their maximal responses.

The invention claimed is:

1. A compound of formula (I) or a pharmaceutically acceptable salt thereof:

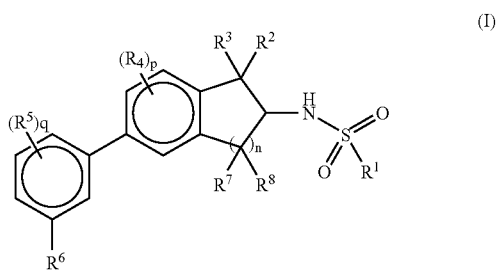

wherein:

R$^1$ is C$_{1-6}$alkyl, haloC$_{1-6}$alkyl, C$_{2-6}$alkenyl, amino, monoC$_{1-4}$alkylamino or diC$_{1-4}$alkylamino;

R$^2$ and R$^3$, which may be the same or different, are hydrogen, halogen, C$_{1-6}$alkyl, haloC$_{1-6}$alkyl, C$_{1-4}$alkoxy, haloC$_{1-4}$alkoxy, cyano or amino;

each R$^4$, which may be the same or different, is C$_{1-6}$alkyl, halogen, haloC$_{1-6}$alkyl, C$_{1-4}$alkoxy, haloC$_{1-4}$alkoxy, cyano, nitro or amino;

p is 0, 1 or 2;

each R$^5$, which may be the same or different, is C$_{1-6}$alkyl, halogen, haloC$_{1-6}$alkyl, C$_{1-4}$alkoxy, haloC$_{1-4}$alkoxy, cyano, nitro or amino;

q is 0, 1 or 2;

R$^6$ is —NR$^{6a}$SO$_2$R$^{6b}$, —NR$^{6a}$C(=O)R$^{6b}$, —NR$^{6a}$(C=O)N(R$^{6c}$)$_2$, —(C=O)R$^{6d}$, —CH$_2$NR$^{6a}$SO$_2$R$^{6b}$, —CH$_2$NR$^{6a}$C(=O)R$^{6b}$, —CH$_2$NR$^{6a}$(C=O)N(R$^{6c}$)$_2$ or —CH$_2$(C=O)R$^{6d}$; where R$^{6a}$ and each R$^{6c}$, which may be the same or different, is hydrogen or C$_{1-6}$alkyl; R$^{6b}$ and R$^{6d}$ are C$_{1-6}$alkyl or haloC$_{1-6}$alkyl; or R$^{6a}$ and R$^{6b}$, or R$^{6a}$ and R$^{6c}$ together with the interconnecting atoms, may form a 5- or 6-membered ring;

n is 1 or 2; and

R$^7$ and R$^8$, which may be the same or different, are hydrogen, halogen, C$_{1-6}$alkyl, haloC$_{1-6}$alkyl, C$_{1-4}$alkoxy, haloC$_{1-4}$alkoxy, cyano or amino.

2. A compound as claimed in claim 1 wherein R$^1$ is C$_{1-6}$alkyl.

3. A compound as claimed in claim 1 wherein R$^2$ and R$^3$, which may be the same or different, are hydrogen, halogen or C$_{1-6}$ alkyl.

4. A compound as claimed in claim 1 wherein when present, each R$^4$, which may be the same or different, is C$_{1-6}$ alkyl or halogen.

5. A compound as claimed in any of claim 1 wherein when present, each R$^5$, which may be the same or different, is C$_{1-6}$ alkyl or halogen.

6. A compound as claimed in claim 1 wherein n is 1.

7. A compound as claimed in claim 1 wherein R$^7$ and R$^8$, which may be the same or different, are hydrogen, halogen or C$_{1-6}$ alkyl.

8. A compound as claimed in claim 1, having a formula (Ia), or a pharmaceutically acceptable salt thereof:

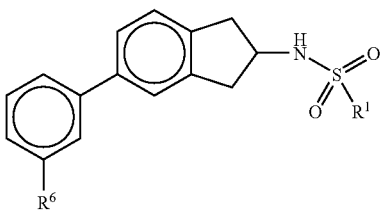

(Ia)

wherein $R^6$ and $R^1$ are as the same as defined in claim 1.

9. A compound as claimed in claim 1 having a formula (Ib) or a pharmaceutically acceptable salt thereof:

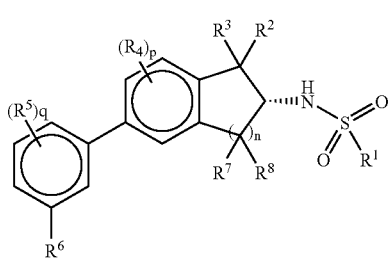

(Ib)

wherein $R^1$, $R^2$, $R^3$, $R^4$, $R^5$, $R^6$, $R^7$, $R^8$, p, q and n are the same as defined in claim 1.

10. A compound as claimed in claim 1 having a formula (Ic) or a pharmaceutically acceptable salt thereof:

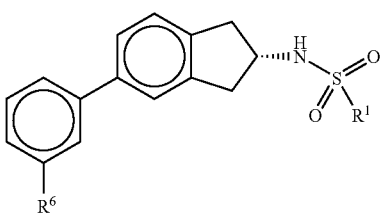

(Ic)

wherein $R^5$, $R^6$ and $R^1$ are the same as defined in claim 1.

11. A compound as claimed in claim 1 which is:
N-(5-{4-[(methylsulfonyl)amino]phenyl}-2,3-dihydro-1H-inden-2-yl)-2-propanesulfonamide;
N-[3-(2-{[(1-methylethyl)sulfonyl]amino}-2,3-dihydro-1H-inden-5-yl)phenyl]acetamide;
N-[5-(3-acetylphenyl)-2,3-dihydro-1H-inden-2-yl]-2-propanesulfonamide;
N-(5-{3-[methyl(methylsulfonyl)amino]phenyl}-2,3-dihydro-1H-inden-2-yl)-2-propanesulfonamide;
N-[5-(3-{[(ethylamino)carbonyl]amino}phenyl)-2,3-dihydro-1H-inden-2-yl]-2-propanesulfonamide;
N-(5-{3-[(ethylsulfonyl)amino]phenyl}-2,3-dihydro-1H-inden-2-yl)-2-propanesulfonamide;
2-methyl-N-[3-(2-{[(1-methylethyl)sulfonyl]amino}-2,3-dihydro-1H-inden-5-yl)phenyl]propanamide;
N-{5-[3-(2-oxopropyl)phenyl]-2,3-dihydro-1H-inden-2-yl}-2-propanesulfonamide;
N-[5-(3-cyanophenyl)-2,3-dihydro-1H-inden-2-yl]-2-propanesulfonamide;
N-{5-[3-(aminomethyl)phenyl]-2,3-dihydro-1H-inden-2-yl}-2-propanesulfonamide;
N-[5-(3-{[(methylsulfonyl)amino]methyl}phenyl)-2,3-dihydro-1H-inden-2-yl]-2-propanesulfonamide;
N-{[3-(2-{[(1-methylethyl)sulfonyl]amino}-2,3-dihydro-1H-inden-5-yl)phenyl]methyl}acetamide;
N-(5-{3-[(2-oxo-1-pyrrolidinyl)methyl]phenyl}-2,3-dihydro-1H-inden-2-yl)-2-propanesulfonamide;
N-{5-[3-(1,1-dioxido-2-isothiazolidinyl)phenyl]-2,3-dihydro-1H-inden-2-yl}-2-propanesulfonamide;
N-(5-{3-[(methylsulfonyl)methyl]phenyl}-2,3-dihydro-1H-inden-2-yl)-2-propanesulfonamide;
3-(2-{[dihydroxy(1-methylethyl)-$\lambda^4$-sulfanyl]amino}-2,3-dihydro-1H-inden-5-yl)-N,N-dimethylbenzenesulfonamide;
3-(2-{[dihydroxy(1-methylethyl)-$\lambda^4$-sulfanyl]amino}-2,3-dihydro-1H-inden-5-yl)benzenesulfonamide;
or a pharmaceutically acceptable salt thereof.

12. A pharmaceutical composition comprising a compound or salt as claimed in claim 1 and a pharmaceutically acceptable carrier or diluent.

13. The composition of claim 12 wherein said compound comprises a mixture of R and S isomers or comprises the essentially pure form of the R or the S isomer.

14. A method of treating or preventing schizophrenia in a human comprising administering an effective amount of a compound as claimed in claim 1 alone or combined with a pharmaceutically acceptable carrier.

* * * * *